United States Patent
Sabir et al.

(10) Patent No.: US 9,999,682 B2
(45) Date of Patent: Jun. 19, 2018

(54) METHOD FOR PREPARING CHITOSAN-COATED MAGNETIC NANOPARTICLES FOR PROTEIN IMMOBILIZATION

(71) Applicant: KING ABDULAZIZ UNIVERSITY, Jeddah (SA)

(72) Inventors: Jamal Sabir M. Sabir, Jeddah (SA); Ahmed Atef Biomy, Jeddah (SA); Fotouh M El-Doiaty, Jeddah (SA); Sherif Edris, Jeddah (SA); Nahid H. Hajrah, Jeddah (SA); Osama A. Abuzinadah, Jeddah (SA); Ahmed Bahieldin, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 165 days.

(21) Appl. No.: 14/983,448

(22) Filed: Dec. 29, 2015

(65) Prior Publication Data

US 2017/0182188 A1 Jun. 29, 2017

(51) Int. Cl.
*A61K 47/06* (2006.01)
*A61K 47/48* (2006.01)
*A61K 49/18* (2006.01)
*G01N 33/543* (2006.01)
*G01N 33/548* (2006.01)

(52) U.S. Cl.
CPC .. *A61K 47/48923* (2013.01); *A61K 47/48861* (2013.01); *A61K 49/1863* (2013.01); *G01N 33/548* (2013.01); *G01N 33/5434* (2013.01); *G01N 33/54346* (2013.01); *G01N 33/54353* (2013.01)

(58) Field of Classification Search
None
See application file for complete search history.

(56) References Cited

U.S. PATENT DOCUMENTS 7,547,473 B2    6/2009   Chen et al.

FOREIGN PATENT DOCUMENTS

CN          103497347        1/2014

OTHER PUBLICATIONS

Jia et al., "In situ preparation of magnetic chitosan/Fe3O4 composite nanoparticles in tiny pools of water-in-oil microemulsion", Reactive & Functional Polymers 66: 1552-1558 (2006). (Year: 2006).*
Li et al., "Preparation and properties of magnetic Fe3O4-chitosan nanoparticles", Journal of Alloys and Compounds 466: 451-456 (2008). (Year: 2008).*
Dung et al., " Preparation and characterization of magnetic nanoparticles with chitosan coating", Journal of Physics: Conference Series 187: 012036 (2009). (Year: 2009).*

* cited by examiner

*Primary Examiner* — Anand U Desai
(74) *Attorney, Agent, or Firm* — Richard C. Litman

(57) ABSTRACT

A method for preparing chitosan-coated magnetic nanoparticles for protein immobilization includes forming ferrous ferric oxide ($Fe_3O_4$) nanoparticles by co-precipitation and coating the nanoparticles with chitosan in the presence of glutaraldehyde. The $Fe_3O_4$ nanoparticles can be coated by dispersing ferrous ferric oxide ($Fe_3O_4$) nanoparticles into a solution comprising chitosan and acetic acid, adding a surfactant, adding excess 50% glutaraldehyde solution, and washing the nanoparticles with a solvent. The chitosan coated ferric oxide ($Fe_3O_4$) nanoparticles can be used to immobilize proteins or other biomolecules.

3 Claims, 5 Drawing Sheets

METHOD FOR PREPARING CHITOSAN-COATED MAGNETIC NANOPARTICLES FOR PROTEIN IMMOBILIZATION

BACKGROUND OF THE INVENTION

1. Field of the Invention

The present invention relates to magnetic nanoparticles, and particularly to magnetic nanoparticles for protein immobilization.

2. Description of the Related Art

Magnetic particles are being increasingly used as carriers for binding proteins, enzymes, and drugs. Such immobilization procedures for proteins and other biologically active compounds have a major impact in different areas of biomedicine and biotechnology. For example, nano magnetic beads or particles are used in various applications in medical, diagnostic and industrial applications. Coupling of proteinaceous sources at the surface of magnetic beads has been achieved by several methods using surface activating material and surface functionalized magnetic particles. Surface activating chemicals, such as ethyl (dimethylaminopropyl) carbodiimide (EDC) react with surface carboxylated magnetic beads and the resulting chemical group is highly reactive with the amino groups in proteins. However, the main disadvantage of this method is the high cost and instability of the EDC compound, which therefore limits the adoption of this technology on a commercial scale.

Coating of magnetic beads provides an alternative avenue for coupling with proteins by providing a wide variety of functional groups (aldehyde, epoxy, etc.) that can be used directly in protein coupling. Chitosan compound was used previously for coating magnetic beads, as a heavy metal ion capture, in water treatment in order to couple various proteins for diagnostic and medical usages. Chitosan β-(1-4)-linked D-glucosamine is the second most abundant material after cellulose and has been widely used in various applications as a biodegradable and environmental friendly material. Chitosan-coated magnetic beads offer a low cost option for large scale production of enzyme-coupled magnetic nanoparticles in various applications. Typically, however, preparation of chitosan-coated magnetic beads often includes activating the magnetic bead's surface by EDC and cross-linking it by glutaraldehyde. While this protocol has been used for large-scale production of magnetic beads, use of EDC renders the process costly.

Reverse phase emulsion is a preparation method for magnetic nanoparticles which facilitates control of the size (diameter) of the magnetic particles. Glutaraldehyde is added directly after the formation of the emulsion. The nanoparticles are then be purified for surface activation and enzyme coupling. Some researchers have activated the surface of chitosan-coated beads by incubating it with a low amount of glutaraldehyde and then added enzyme after washing. The disadvantage of this method, however, is the intra cross-linking between amino groups across magnetic beads after activation. This type of cross-linking can yield clotted beads which can affect the homogeneity in the diameter of the beads.

Thus, a method for preparing chitosan-coated magnetic nanoparticles for protein immobilization solving the aforementioned problems is desired.

SUMMARY OF THE INVENTION

A method for preparing chitosan-coated magnetic nanoparticles for protein immobilization includes forming ferrous ferric oxide ($Fe_3O_4$) nanoparticles by co-precipitation and coating the nanoparticles with chitosan in the presence of glutaraldehyde. The $Fe_3O_4$ nanoparticles can be coated by dispersing ferrous ferric oxide ($Fe_3O_4$) nanoparticles into a solution comprising chitosan and acetic acid, adding a surfactant while vigorously stirring, adding excess 50% glutaraldehyde solution, and washing the nanoparticles with a solvent. The chitosan coated ferric oxide ($Fe_3O_4$) nanoparticles can be used to immobilize proteins or other biomolecules.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method for preparing chitosan-coated magnetic nanoparticles for protein immobilization includes forming ferrous ferric oxide ($Fe_3O_4$) nanoparticles by co-precipitation and coating the nanoparticles with chitosan in the presence of high amounts of glutaraldehyde (e.g., 50% glutaraldehyde solution). Chitosan covalently binds to surfaces of the magnetic $Fe_3O_4$ nanoparticles to form chitosan-coated magnetic nanoparticles or aldehyde-activated chitosan-magnetic nanoparticles. The chitosan coating of the $Fe_3O_4$ nanoparticles does not result in a phase change. The $Fe_3O_4$ nanoparticles and chitosan-coated magnetic nanoparticles are regular spheres, having a mean diameter of 20 nm.

The present inventors have determined that use of excess amounts of glutaraldehyde avoids the need for additional, costly, or undesirable treatment with other chemicals (e.g., EDC) which are traditionally used for activating the surface of nanoparticles of appropriate structure and diameter. The chitosan coated magnetic nanoparticles can be used directly in amino group-based protein conjugation. The chitosan coated magnetic nanoparticles possess good thermal stability and a long shelf-storage life.

Chitosan is a linear polysaccharide composed of randomly distributed β-(1-4)-linked D-glucosamine (deacetylated unit) and N-acetyl-D-glucosamine (acetylated unit). A polysaccharide is a polymeric carbohydrate molecule composed of long chains of monosaccharide units bound together by glycosidic linkages. Glutaraldehyde is an organic compound with the formula $CH_2(CH_2CHO)_2$. A nanoparticle is a microscopic particle with at least one dimension less than 100 nm.

The ferrous ferric oxide ($Fe_3O_4$) magnetic nanoparticles are formed in a solution of ferrous and ferric chloride by a co-precipitation method. In detail, ferric/ferrous chlorides (2:1 molar ratio) are dissolved in water to form an iron-containing solution, then heated to 80° C. with alkaline solution, such as NaOH (30%). The alkaline solution is added to adjust pH to a pH of about 8.5 to about 10. The reaction is maintained for about 2 hours to provide magnetic nanoparticles of $Fe_3O_4$. The magnetic nanoparticles are then washed several times with deionized water and dried at 80° C. in an oven.

Figure 1:
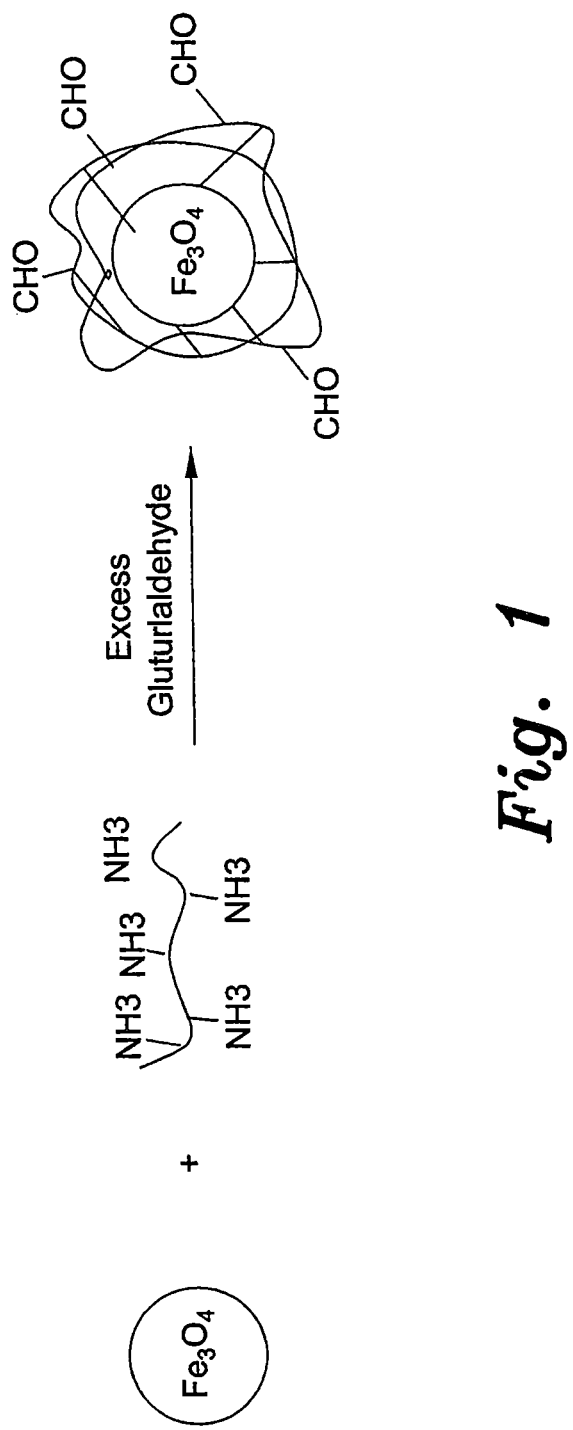
FIG. 1 is a schematic representation of the chitosan-coating reaction process.

The magnetic nanoparticles can be dispersed in chitosan solution (e.g., 1% chitosan solution) and acetic acid (e.g., 1% acetic acid). The dispersion is added to paraffin oil with Span® 20 (Sorbitan, monododecanoate) as surfactant. A water-in-oil dispersion is obtained by vigorous ultrasonic stirring for 30 min. Then, an excess amount of concentrated glutaraldehyde solution is added and the dispersion is left for 3 hours at room temperature under continuous stirring. Then, the dispersion is left overnight at 4° C. to ensure a complete reaction between amino groups and glutaraldehyde. The complete reaction includes 1) cross-linking between chitosan to form coated magnetic beads; and 2) protein coupling (as shown in FIG. 1) facilitated by the availability of an excess amount of glutaraldehyde as the functional group. This method for coating the magnetic nanoparticles can be referred to as reverse-phase suspension cross-linking. The beads are then washed several times with methanol, acetone and water to remove all paraffin oil residues and then dried in an oven.

Protein coupling with the chitosan coated magnetic nanobeads can be accomplished as a one-step method by simply mixing the required amount of protein of choice (e.g., BSA (bovine serum albumin) for saturation determination) directly to the beads for about 16 hours at about 4° C. for best results. The immobilized biomolecules can be used directly for bioassays in a diagnostic kit, MRI contrast agents for imaging or for modifying target molecules or cells.

The following examples will further illustrate the synthesis process of chitosan coated with the magnetic nano-beads/nanoparticles.

EXAMPLE 1

Preparation of Magnetic $Fe_3O_4$ Nanoparticles

In a container, 2.7 g ferric chloride (hexahydrate) and 3.9 g ferrous chloride (tetrahydrate) (2:1 molar ratio) were dissolved in water to form an iron-containing solution and heated to 80° C. Then about 50 ml solution of NaOH (30%) was added to the solution to adjust the pH to 8.5-10 and the reaction was maintained for about 2 hours to obtain magnetic nanoparticles of $Fe_3O_4$. Finally, the magnetic nanoparticles were washed several times with deionized water and dried at 80° C. in an oven.

EXAMPLE 2

Coating of Magnetic $Fe_3O_4$ Nanoparticles

Figure 2:
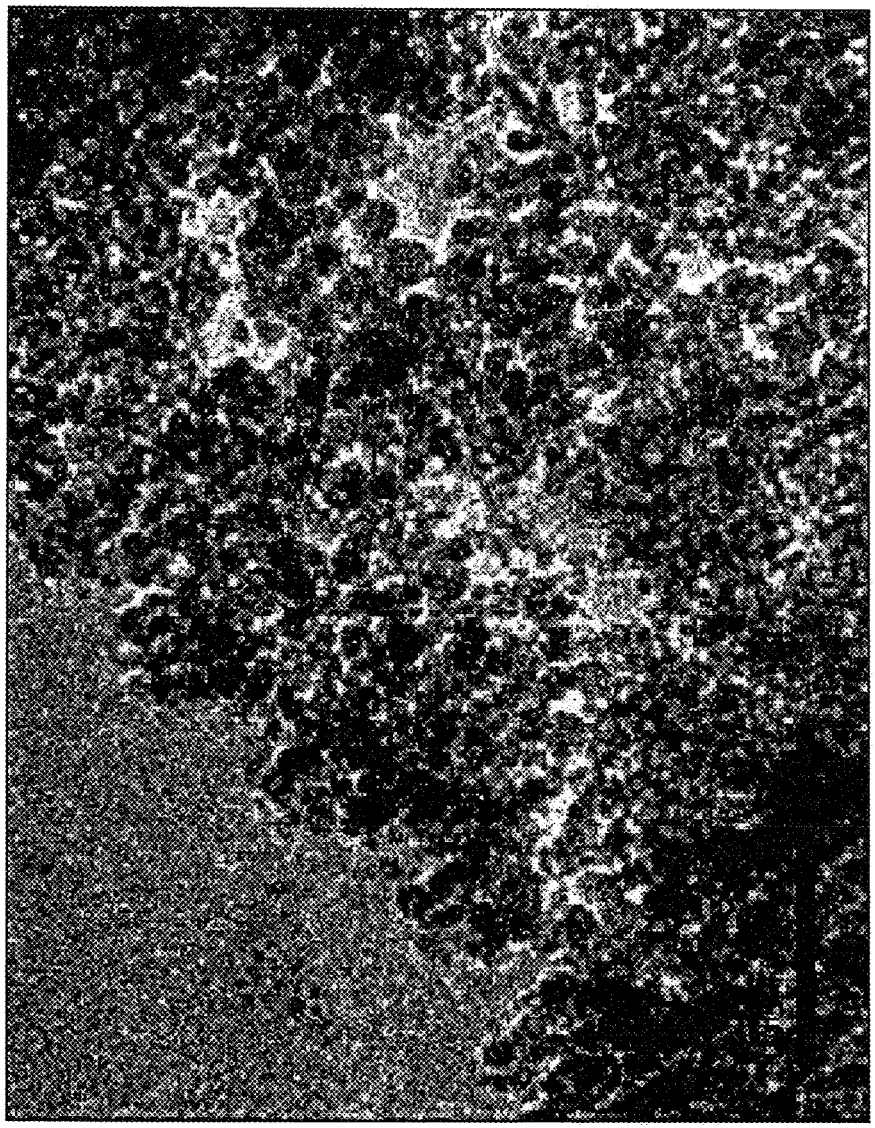
FIG. 2 shows the Transmission Electron Microscopy (TEM) analysis of the chitosan-coated magnetic nanoparticles.
Figure 3A:
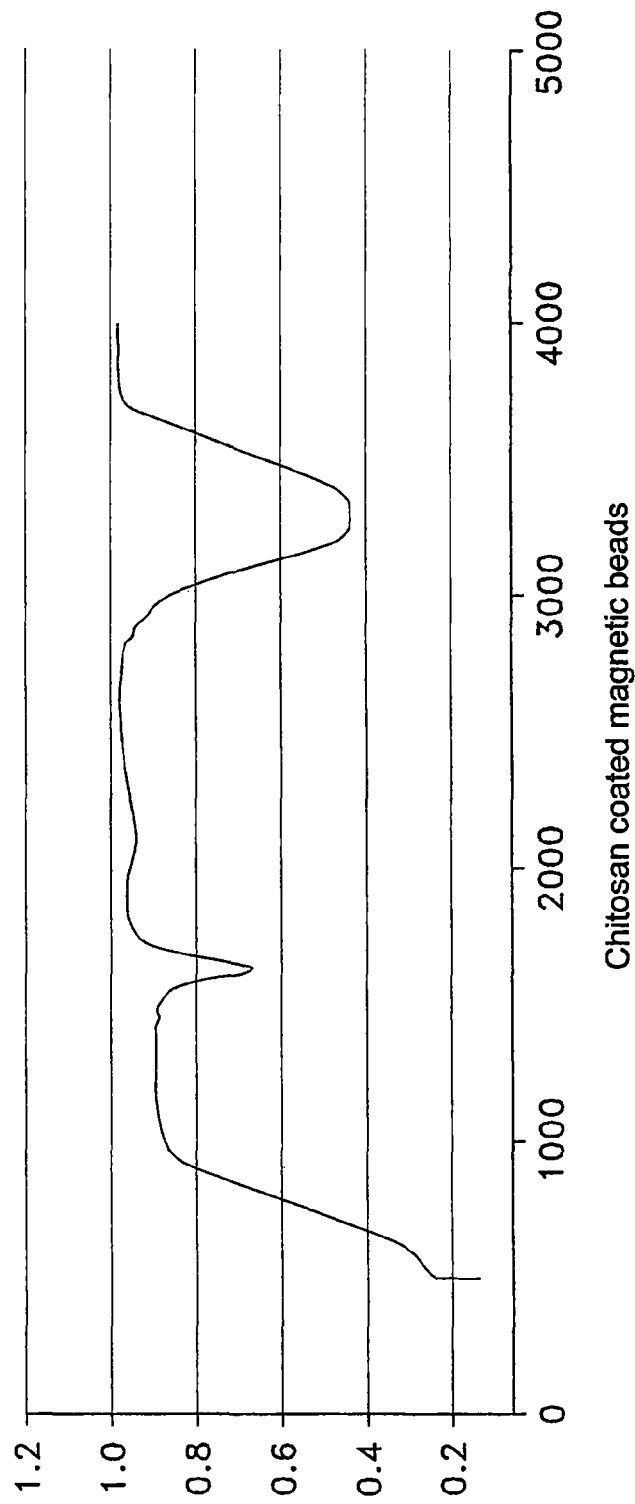
FIG. 3A shows a FTIR absorbance graph for chitosan-coated magnetic nanoparticles.
Figure 3B:
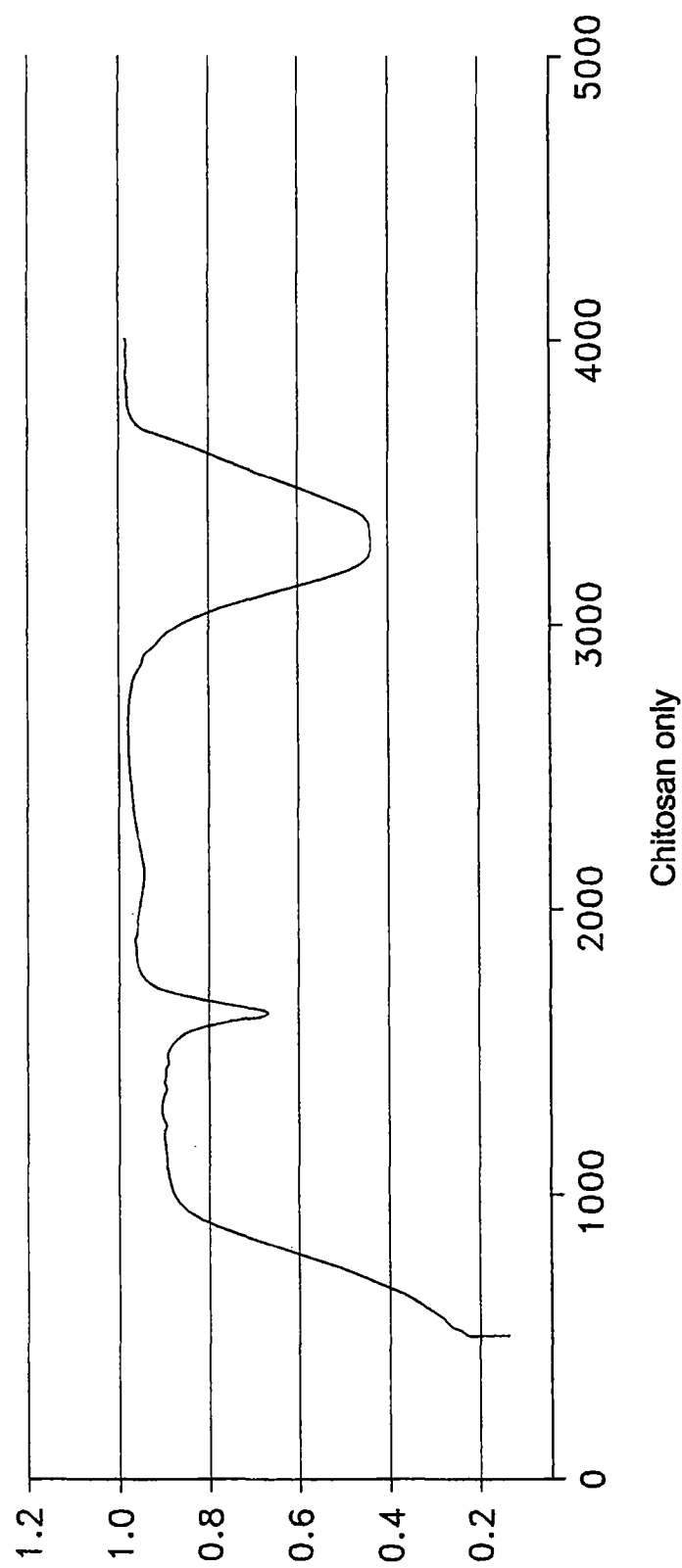
FIG. 3B shows a FTIR absorbance graph for chitosan only.
Figure 3C:
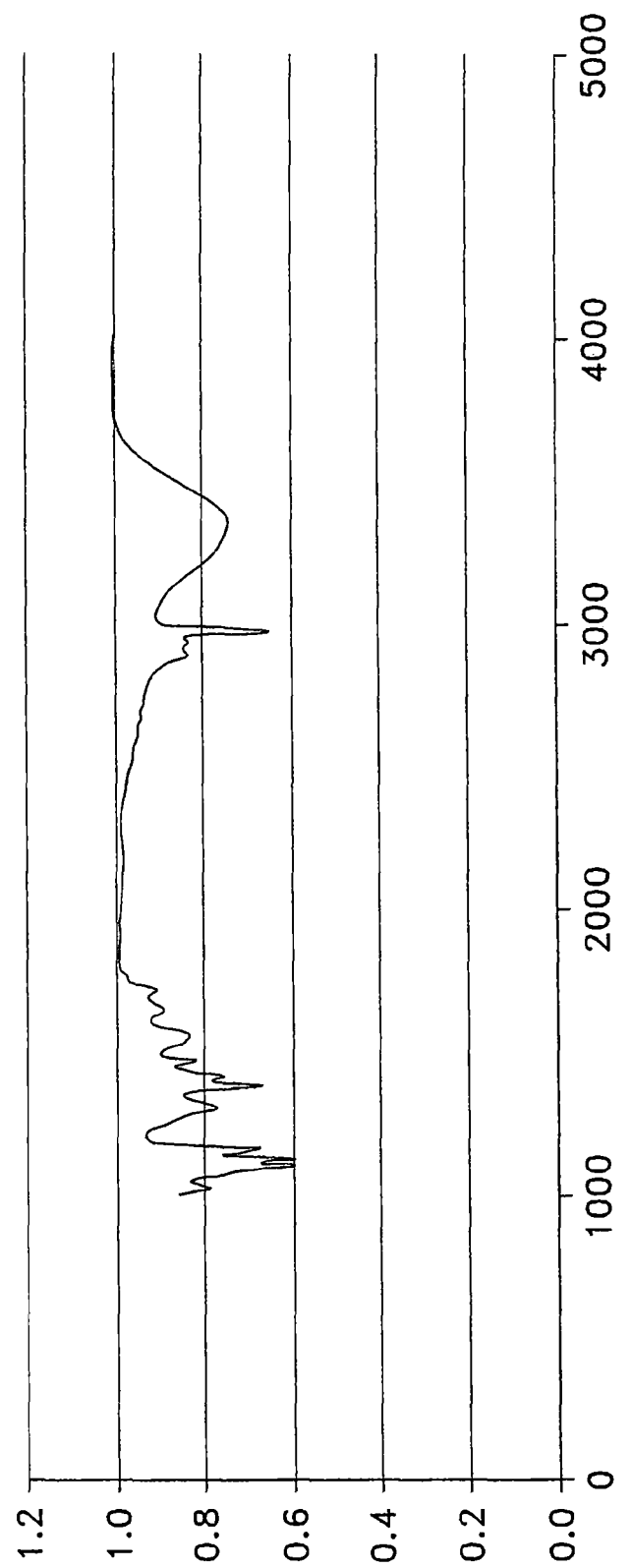
FIG. 3C shows a FTIR absorbance graph for magnetic beads only.

Low-molecular-weight chitosan (≥85%) deacetylation was prepared as described previously in the prior art (Yateendra et al., 2012). Chitosan-coated magnetic nanoparticles were obtained by dispersing 0.5 g of magnetic nanoparticles in 30 ml 1% chitosan solution and 1% acetic acid followed by sonication for 15 minutes. The dispersion was added to 70 ml paraffin oil and 0.5 g of SPAN® 20 (sorbitan monododecanoate), which was used as surfactant. A water-in-oil dispersion was obtained by vigorous ultrasonic stirring for 30 min. Then, 5 ml of 50% glutaraldehyde solution ($CH_2(CH_2CHO)_2$) was added for 3 hours at room temperature under magnetic stirring. The solution was then maintained overnight at 4° C. Magnetic nanobeads, were then washed several times by methanol, acetone and water to remove paraffin oil residues, then dried in an oven at 80° C. for 12 h. As shown in FIG. 2, the average diameter of the resulting beads, determined by electron microscopy, was found to be about 20 nm. The resulting beads were analyzed also by FTIR as shown in FIGS. 3A, 3B and 3C to establish that the beads had been coated with chitosan.

EXAMPLE 3

Protein Coupling with Chitosan Coated Magnetic Nano Beads

About 100 mg of chitosan coated magnetic nanobeads was dispersed in 9 ml of PBS buffer (pH 7.0) and then mixed with 1 ml BSA (bovine serum albumin) at different concentrations (i.e., 1, 5, 10, 15, 20, 30 and 50 mg) dissolved in PBS buffer. The mixture was maintained for 16 hours at 4° C. under stirring condition (120 rpm). Then the magnetic particles were collected using a strong magnet. The supernatant was used to measure the protein concentration using Bradford method and the results were compared to the BSA standard curve. Then, the unbounded protein was measured using the Bradford method as shown in Table 1 below.

TABLE 1

Bound and Unbounded Protein as measured using Bradford method

| Total protein (mg) (Bradford) | Unbound | Bound |
|---|---|---|
| 1 | 0 | 1 |
| 5 | 0 | 5 |
| 10 | 2 | 8 |
| 15 | 3 | 12 |
| 20 | 8 | 12 |
| 30 | 17 | 13 |
| 50 | 36 | 14 |

The results indicated that an amount of 15 mg of protein for 100 mg of beads was the best concentration for the highest saturation.

It is to be understood that the present invention is not limited to the embodiments described above, but encompasses any and all embodiments within the scope of the following claims.

We claim:

1. A method for preparing chitosan-coated magnetic Nanoparticles and coupling to a protein for protein immobilization, comprising:
    forming ferrous ferric oxide ($Fe_3O_4$) nanoparticles;
    dispersing the ferrous ferric oxide ($Fe_3O_4$) nanoparticles into a solution comprising chitosan and acetic acid to form a dispersion;
    adding an oil and a surfactant to the dispersion while vigorously stirring to form a water-in-oil dispersion;
    adding 5 mL of excess 50% glutaraldehyde solution to the water-in-oil dispersion to form a reaction mixture, wherein a cross-linking reaction occurs between an amino group of the chitosan and an aldehyde group of the glutaraldehyde;
    maintaining the reaction mixture overnight at 4° C. to form the chitosan-coated magnetic nanoparticles;
    coupling the chitosan-coated magnetic nanoparticles with a protein molecule, comprising mixing the chitosan-coated magnetic nanoparticles directly with a protein molecule held in a buffer solution at pH 7.0; and
maintaining the mixture for 16 hours at 4° C. under stirring conditions.

2. The method for preparing chitosan-coated magnetic nanoparticles for protein immobilization according to claim 1, further comprising washing the chitosan-coated magnetic nanoparticles and drying the chitosan-coated magnetic nanoparticles in an oven at 80° C.

3. The method for preparing chitosan-coated magnetic nanoparticles for protein immobilization according to claim 1, wherein the oil is paraffin oil and the surfactant is sorbitan monododecanoate.

* * * * *